United States Patent
Stölting

(10) Patent No.: US 7,235,668 B2
(45) Date of Patent: Jun. 26, 2007

(54) PROCESS FOR THE PREPARATION OF THIOALKYLAMINE DERIVATIVES

(75) Inventor: Jörn Stölting, Köln (DE)

(73) Assignee: Bayer CropScience AG, Monheim (DE)

( * ) Notice: Subject to any disclaimer, the term of this patent is extended or adjusted under 35 U.S.C. 154(b) by 429 days.

(21) Appl. No.: 10/515,441

(22) PCT Filed: May 12, 2003

(86) PCT No.: PCT/EP03/04911

§ 371 (c)(1), (2), (4) Date: Nov. 22, 2004

(87) PCT Pub. No.: WO03/099777

PCT Pub. Date: Dec. 4, 2003

(65) Prior Publication Data

US 2005/0182275 A1 Aug. 18, 2005

(30) Foreign Application Priority Data

May 24, 2002 (EP) .................................. 02011545

(51) Int. Cl.
*C07C 319/14* (2006.01)
*C07C 323/25* (2006.01)
*C07D 277/74* (2006.01)

(52) U.S. Cl. ...................... 548/165; 548/174; 564/341; 564/500; 564/501

(58) Field of Classification Search ................ 548/165, 548/174; 564/341, 500, 501
See application file for complete search history.

(56) References Cited

U.S. PATENT DOCUMENTS

| 2,689,867 A | | 9/1954 | Mahan ........................ 260/563 |
| 2,912,357 A | * | 11/1959 | Harman et al. ............. 514/367 |
| 3,318,953 A | | 5/1967 | Wehrmeister et al. ....... 260/558 |
| 5,405,947 A | * | 4/1995 | Hoppe et al. ................. 534/618 |
| 5,507,840 A | | 4/1996 | Schrell et al. .................. 8/532 |
| 6,639,109 B1 | * | 10/2003 | Sanpei et al. ................ 564/501 |

FOREIGN PATENT DOCUMENTS

| DE | 2 045 905 | 3/1972 |
| EP | 1 216 988 A | 6/2002 |
| JP | 59-231064 | 12/1984 |
| WO | 01/23350 A | 4/2001 |

OTHER PUBLICATIONS

Bull. Soc. Chim. Fr. (month unavailable) 1967, p. 3637-3639, Jean-Louis Larige et al, "Préparation de thiazolidines á partir d'aziridines."

J. Med. Chem. 8, (month unavailable) 1965, p. 762-766, G. Richard Handrick et al, "Potential Antiradiation Drugs. II. 2-Amino-1-alkanethiols, 1-Amino-2-alkanethiols, 2-Thiazolines, and 2-Thiazoline-2-thiols".
Nippon Kagaku Kaishi, (month unavailable) 1979, p. 149-151, Hachiro Yamaguchi et al, A Novel Synthesis of 2-Aminoethanethiol and its Derivatives (see abstract p. 151).
J. Org. Chem. 57 (month unavailable) 1992, p. 6257-6265 Graham S. Poindexter et al, "The Use of 2-Oxazolidinones as Latent Aziridine Equivalents. 2. Aminoethylation of Aromatic Amines, Phenols, and Thiophenols".
J. Med. Chem. 27, (month unavailable) 1984, p. 1354-1357, Stephen R. Padgette et al, "Antihypertensive Activities of Phenyl Aminoethyl Sulfides, a Class of Synthetic Substrates for Dopamine β-Hydroxylase".
A Fränkel et al: Berichte Der Deutschen Chemischen Gesellschaft, vol. 51, 1918, pp. 1654-1662, XP002256757.

* cited by examiner

*Primary Examiner*—Fiona T. Powers
(74) *Attorney, Agent, or Firm*—Richard E. L. Henderson

(57) ABSTRACT

The present invention relates to a novel process for the preparation of compounds of the formula (I)

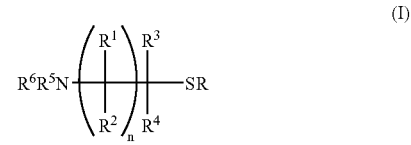

by reacting in a first step amino alcohols of the formula (II)

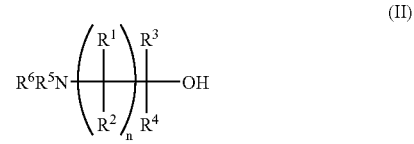

with oleum to give sulphuric acid esters of the general formula (III)

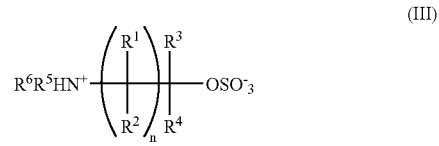

and by reacting these sulphuric acid esters in a second step with mercaptans or salts thereof of the general formula (IV)

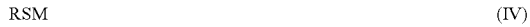

wherein in each formula, where applicable, $R^1$, $R^2$, $R^3$, $R^4$, $R^5$, $R^6$, R, n and M have the meanings given in the disclosure,
in the presence of a diluent and in the presence of a base.

10 Claims, No Drawings

PROCESS FOR THE PREPARATION OF THIOALKYLAMINE DERIVATIVES

The present patent application has been filed under 35 U.S.C. 371 as a national stage application of PCT/EP03/04911, filed May 12, 2003, which was published in English as International Patent Publication WO 03/099777 on Dec. 4, 2003, which is entitled to the right of priority of European Patent Application 02011545.7, filed May 24, 2002.

The present invention relates to a novel process for the preparation of known thio-alkylamine derivatives.

Because of their chemical structure thioalkylamine derivatives can be divided into two groups, thiols and sulphides. For the preparation of both classes the methods discussed below have been described.

A first method for the preparation of thiols is based on the hydrolytic cleavage of thiazoline or thiazolidinone derivatives (cf. e.g. J. Med. Chem. 1965, 8, 762; JP 59-231064, Bull. Soc. Chim. Fr. 1967, 3637). As thiazoline or thiazolidinone derivatives have to be prepared first via several reaction steps the overall yield of this method is very low.

Thiols can be obtained furthermore by a process comprising reacting sulphates of amino alcohols with ammonium sulphide (cf. e.g. Nihon Kagaka Kaishi 1979 149). This method requires long reactions times in a sealed reaction vessel, which causes high costs because of the required production plants having low productivity.

The reaction of oxazoline- or oxazolidinone derivatives with thiols is a method for the preparation of sulphides (cf. e.g. J. Org. Chem. 1992, 57, 6257; J. Med. Chem. 1984, 27, 1354). A hydrolytic process is required to obtain reaction products as amides according to this method. However, no reaction is observed, if the oxazolidine ring of the starting compounds is e.g. alkyl substituted. Furthermore, only aromatic sulphides can be prepared using this method because of the acidity of the mercaptans.

The hydrolytic cleavage of amides, which can be obtained by reaction of amino alcohols with mercaptans in the presence of carboxylic acids, also furnishes sulphides (cf. e.g. DE-OS 14 93 534). This method has to be carried out at high temperature and under pressure using long reaction times and is therefore restricted to the synthesis of sulphides. Additionally a hydrolytic step is required to obtain the reaction products from amides.

The reaction of aziridines with sulphur compounds like mercaptans represents a method for preparing of sulphides and thiols (cf e.g. Tetrahedron 1992, 48, 2359; Tetrahedron Lett. 1983, 24, 2131). High demands on safety requirements have to be made for industrial scale production using this method, because highly toxic and possibly instable aziridines have to be prepared and isolated.

A method for the conversion of thioalkylalcohols into thioalkylamines is represented by the Ritter reaction with subsequent hydrolytic cleavage (cf. e.g. DE-OS 20 45 905). This method employs hydrocyanic acid in excess, which must be handled with the utmost caution. In the case that nitriles which can be easily handled are employed the hydrolytic process causes problems.

A further method for the preparation of thioalkylamine derivatives uses as starting material amino alcohols which are reacted with sulphuric acid to give the corresponding esters in a first step (cf WO 01/23350). After evaporation to dryness this esters are further converted by reaction with mercaptans. The required evaporation after the first reaction step causes problems when this process is employed to a large scale production.

We have now found that compounds of the formula (I)

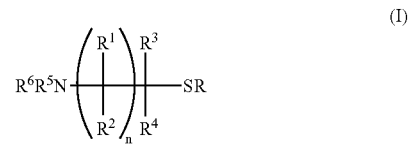

(I)

in which $R^1$ and $R^2$ in each case independently of one another represent hydrogen, $C_1$-$C_4$-alkyl, $C_3$-$C_8$-cycloalkyl, $C_3$-$C_8$-cycloalkyl-$C_1$-$C_4$-alkyl, hydroxy-$C_1$-$C_4$-alkyl; unsubstituted or mono- to pentasubstituted phenyl, where the substituents are identical or different and are selected from the group consisting of halogen, cyano, nitro, $C_1$-$C_4$-allyl $C_3$-$C_8$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, carboxyl, $C_1$-$C_4$-alkoxycarbonyl, $C_1$-$C_4$-alkoxy-$C_1$-$C_4$-alkyl, $C_1$-$C_4$-alkylcarbonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl, halo-$C_1$-$C_4$-alkylsulfonyl, halo-$C_1$-$C_4$-alkylcarbonyl, phenylcarbonyl phenoxycarbonyl, amino, $C_1$-$C_4$-alkylamino and di-($C_1$-$C_4$-alkyl)-amino (where the alkyl groups can be identical or different); phenyl, which is substituted at two adjacent carbon atoms by $C_3$-$C_4$-alkylene or $C_1$-$C_2$-alkylenedioxy; unsubstituted or mono- to pentasubstituted phenyl-$C_1$-$C_4$-alkyl, where the substituents are identical or different and are selected from the group consisting of halogen, cyano, nitro, $C_1$-$C_4$-alkyl, $C_3$-$C_8$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl and halo-$C_1$-$C_4$-alkylsulfonyl;

$R^3$ and $R^4$ independently of one another represent hydrogen or $C_1$-$C_4$-alkyl, $R^5$ and $R^6$ independently of one another represent hydrogen, $C_1$-$C_4$-alkyl, unsubstituted or mono- to pentasubstituted phenyl, where the substituents are identical or different and are selected from the group consisting of halogen, cyano, nitro, $C_1$-$C_4$-alkyl, $C_3$-$C_8$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl and halo-$C_1$-$C_4$-alkylsulfonyl; unsubstituted or mono- to pentasubstituted phenyl-$C_1$-$C_4$-alkyl, where the substituents are identical or different and are selected from the group consisting of halogen, cyano, nitro, $C_1$-$C_4$-alkyl, $C_3$-$C_8$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsufinyl and halo-$C_1$-$C_4$-alkylsulfonyl, R represents unsubstituted or mono- or polysubstituted $C_1$-$C_{12}$-alkyl, where the substituents are identical or different and ae selected from the group consisting of halogen, hydroxy, $C_1$-$C_4$-alkoxy, halo-$C_1$-$C_4$-alkoxy, $C_1$-$C_4$-alkylthio, $C_1$-$C_4$-alkylsulfinyl and $C_1$-$C_4$-alkylsulfonyl; unsubstituted or mono- or polysubstituted $C_3$-$C_8$-cycloalkyl or $C_3$-$C_8$-cycloalkyl-$C_1$-$C_4$-alkyl, where the substituents are identical or different and are selected from the group consisting of halogen, $C_1$-$C_4$-alkyl and $C_1$-$C_4$-alkoxy; unsubstituted or mono- to pentasubstituted phenyl, where the substituents are identical or different and are selected from the group consisting of halogen, $C_1$-$C_6$-alkyl, $C_3$-$C_8$-cycloalkyl, $C_1$-$C_4$-alkoxy, halo-$C_1$-$C_4$-alkyl, halo-$C_1$-$C_4$-alkoxy, unsubstituted or mono- to pentasubstituted phenyl-$C_1$-$C_4$-alkyl, where the substituents are identical or different and are selected from the group consisting of halogen and $C_1$-$C_4$-alkyl; naphthyl; unsubstituted or mono- or polysubstituted heteroaryl, where the substituents are identical or different and are selected from the group consisting of halogen, $C_1$-$C_4$-alkyl, $C_1$-$C_4$-alkoxy, unsubstituted or mono- to pentasubstituted phenyl where the substituents are identical or different and are selected from the group consisting of halogen and $C_1$-$C_4$-alkyl, n represents 1, 2, 3, 4, 5, 6, 7 or 8, where the group $C(R^1)R^2$ may be identical or different, when n is greater than 1, and when n represents 1, $R^1$ and $R^2$ furthermore together represent $C_2$-$C_5$-alkylene,
$R^1$ furthermore represents together with $R^3$ or $R^5$ $C_3$-$C_5$-alkylene,
$R^3$ and $R^4$ furthermore together represent $C_4$-$C_6$-alkylene,
$R^3$ and $R^5$ furthermore together represent $C_2$-$C_4$-alkylene,
$R^5$ and $R^6$ furthermore together represent $C_4$-$C_6$-alkylene, are obtained by reacting in a first step amino alcohols of the formula (II)

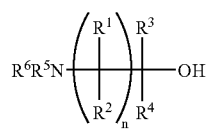

(II)

in which
$R^1, R^2, R^3, R^4, R^5, R^6$ and n have the above given meanings, with oleum to give sulphuric acid esters of the general formula (m)

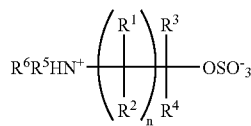

(III)

in which
$R^1, R^2, R^3, R^4, R^5, R^6$ and n have the above given meanings, and by reacting these sulphuric acid esters in a second step with mercaptans or salts thereof of the general formula (IV)

RSM    (IV)

in which
R has the above given meanings, and
M represents hydrogen, ammonium or an alkali metal atom, in the presence of a base and preferably in the presence of a diluent.

Surprisingly, using the process according to the invention, the thioalkylamines of the formula (I) can be obtained in a simple manner in a very good space-time yield.

The reaction according to the invention therefore has the advantage of an increased reaction rate. This leads to the technical advantage of a high space-time yield. The process according to the invention has the further advantage that the solution of the intermediates of formula (III) need not to be evaporated to dryness. The reaction mixture can be stirred at any time of the process which decreases the risk of a breaking reaction vessel in industrial plants.

DETAILED DESCRIPTION OF THE PROCESS ACCORDING TO THE INVENTION

The course of the reaction of the process according to the invention can be outlined by the following general reaction scheme:

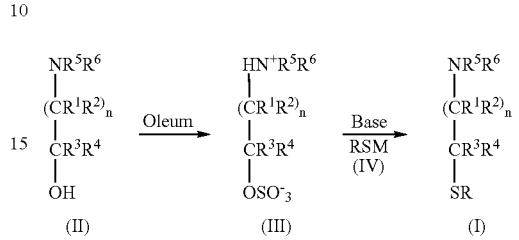

The formula (II) provides a general definition of the amino alcohols required as starting materials for carrying out the first step of the process according to the invention.

Preferred as starting material are amino alcohols of the formula (O, in which
$R^1$ and $R^2$ in each case independently of one another represent hydrogen, $C_1$-$C_4$-alkyl, $C_3$-$C_6$-cycloalkyl, $C_3$-$C_6$-Cycloalkyl-$C_1$-$C_2$-alkyl, hydroxy-$C_1$-$C_4$-alkyl; unsubstituted or mono- to pentasubstituted phenyl, where the substituents are identical or different and are selected from the group consisting of fluorine, chlorine, bromine, iodine, cyano, nitro, $C_1$-$C_4$-alkyl $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, carboxyl, $C_1$-$C_4$-alkoxycarbonyl, $C_1$-$C_4$-alkoxy-$C_1$-$C_4$-alkyl, $C_1$-$C_4$-alkylcarbonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl, halo-$C_1$-$C_4$-alkylsulfonyl, halo-$C_1$-$C_4$-alkylcarbonyl, each having 1 to 9 identical or different fluorine, chlorine and/or bromine atoms, phenylcarbonyl, phenoxycarbonyl, amino, $C_1$-$C_4$-alkylamino and di-($C_1$-$C_4$-alkyl)-amino (where the alkyl groups can be identical or different); phenyl, which is substituted at two adjacent carbon atoms by $C_3$-$C_4$-alkylene or $C_1$-$C_2$-alkylenedioxy; unsubstituted or mono- to pentasubstituted phenyl-$C_1$-$C_2$-alkyl, where the substituents are identical or different and are selected from the group consisting of fluorine, chlorine, bromine, iodine, cyano, nitro, $C_1$-$C_4$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl and halo-$C_1$-$C_4$-alkylsulfonyl, each having 1 to 9 identical or different fluorine, chlorine and/or bromine atoms;

$R^3$ and $R^4$ independently of one another represent hydrogen or $C_1$-$C_4$-alkyl, $R^5$ and $R^6$ independently of one another represent hydrogen, $C_1$-$C_4$-alkyl, unsubstituted or mono- to pentasubstituted phenyl, where the substituents are identical or different and are selected from the group consisting of fluorine, chlorine, bromine, iodine, cyano, nitro, $C_1$-$C_4$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfinyl halo-$C_1$-$C_4$-alkyl, halo-$C_1$-$C_4$-alkoxy, halo-$C_1$-$C_4$-alkylthio, halo-$C_1$-$C_4$-alkylsulfinyl and halo-$C_1$-$C_4$-alkylsulfonyl, each having 1 to 9 identical or different fluorine, chlorine and/or bromine atoms; unsubstituted or mono- to pentasubstituted phenyl-$C_1$-$C_2$-alkyl, where the substituents are identical or different and are selected from the group consisting of fluorine, chlorine, bromine, iodine, cyano, nitro, $C_1$-$C_4$-alkyl, $C_3$-$C_8$-cycloakyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsufinyl and halo-$C_1$-$C_4$-alkylsulfonyl, each having 1 to 9 identical or different fluorine, chlorine and/or bromine atoms;

n represents 1, 2, 3, 4, 5 or 6, where the group $C(R^1)R^2$ may be identical or different, when n is greater than 1, and when n represents 1, $R^1$ and $R^2$ furthermore together represent $C_2$-$C_5$-alkylene, $R^1$ furthermore represents together with $R^3$ or $R^5$ $C_3$-$C_5$-alkylene, $R^3$ and $R^4$ furthermore together represent $C_4$-$C_6$-alkylene, $R^3$ and $R^5$ furthermore together represent $C_2$-$C_4$-alkylene, $R^5$ and $R^6$ furthermore together represent $C_4$-$C_6$-alkylene.

Particularly preferred as starting material are amino alcohols of the formula (II), in which $R^1$ and $R^2$ in each case independently of one another represent hydrogen, methyl, ethyl, n-, i-propyl, n-, i-, s-, t-butyl, cyclopropyl, cyclobutyl, cyclopentyl cyclohexyl, cyclopropylmethyl, cyclobutylmethyl, cyclopentylmethyl cyclohexylmethyl, cyclopropylethyl, cyclobutylethyl, cyclopentylethyl, cyclohexylethyl, hydroxymethyl, hydroxyethyl; unsubstituted or mono- to trisubstituted phenyl, where the substituents are identical or different and are selected from the group consisting of fluorine, chlorine, bromine, iodine, cyano, nitro, methyl, ethyl n-, i-propyl, n-, i-, s-, t-butyl, cyclopropyl cyclobutyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfonyl n-, i-, s-, t-butylsulfinyl methylsulfonyl, ethylsulfonyl, n-, i-propylsulfonyl, n-, i-, s-, t-butylsulfonyl trifluoromethyl, trichloromethyl, difluoromethyl dichloromethyl, difluorochloromethyl, fluorodichloromethyl, trifluoromethoxy, trichloromethoxy, difluoromethoxy, dichloromethoxy, difluorochloromethoxy, fluorodichloromethoxy, trifluoro-methylthio, trichloromethylthio, difluoromethylthio, dichloromethylthio, difluorochloromethylthio, fluorodichloromethylthio, trifluoromethylsulfinyl trichloromethylsulfinyl, difluoromethylsulfinyl, dichloromethylsulfinyl, difluorochloromethylsulfinyl, fluorodichloromethylsulfinyl, trifluoromethylsulfonyl, trichloromethylsulfonyl, difluoromethylsulfonyl, dichloromethylsulfonyl difluorochloromethylsulfonyl fluorodichloromethylsulfonyl, trifluoromethylcarbonyl carboxyl, methoxycarbonyl, etioxycarbonyl, methoxymethyl ethoxyethyl, methoxyethyl, ethoxymethyl, methylcarbonyl, ethylcarbonyl, phenylcarbonyl, phenoxycarbonyl, amino, methylamino, ethylamino, propylamino, dimethylamino, diethylamino; phenyl, which is substituted at two adjacent carbon atoms by —$(CH_2)_3$—, —$(CH_2)_4$—, —$OCH_2O$—, —$O(CH_2)_2O$—; in each case unsubstituted or mono- to trisubstituted benzyl or phenylethyl, where in each case the substituents are identical or different and are selected from the group consisting of fluorine, chlorine, bromine, iodine, cyano, nitro, methyl ethyl n-, i-propyl, n-, i-, s-, t-butyl, cyclopropyl, cyclobutyl cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfinyl, n-, i-, s-, t-butylsulfinyl, methylsulfonyl, ethylsulfonyl n-, i-propylsulfonyl, n-, i-, s-, t-butylsulfonyl, trifluoromethyl, trichloromethyl, difluoromethyl, dichloromethyl, difluorochloromethyl, fluorodichloromethyl trifluoromethoxy, trichloromethoxy, difluoromethoxy, dichloromethoxy, difluorochloromethoxy, fluorodichloromethoxy, trifluoromethylthio, trichloromethylthio, difluoromethylthio, dichloromethylthio, difluorochloromethylthio, fluorodichloromethylthio, trifluoromethylsulfinyl, trichloromethylsulfinyl, difluoromethylsulfinyl, dichloromethylsulfinyl difluorochloromethylsulfinyl fluorodichloromethylsulfinyl, trifluoromethylsulfonyl, trichloromethylsulfonyl difluoromethylsulfonyl, dichloromethylsulfonyl difluorochloromethylsulfonyl, fluorodichloromethylsulfonyl;

$R^3$ and $R^4$ independently of one another represent hydrogen, methyl, ethyl, n-, i-propyl, n-, i-, s-, t-butyl, $R^5$ and $R^6$ independently of one another represent hydrogen, methyl, ethyl, n-, i-propyl, n-, i-, s-, t-butyl, unsubstituted or mono- to trisubstituted phenyl, where the substituents are identical or different and are selected from the group consisting of fluorine, chlorine, bromine, iodine, cyano, nitro, methyl ethyl, n-, i-propyl n-, i-, s-, t-butyl, cyclopropyl, cyclobutyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, t-butylsulfinyl, n-, i-propylsulfinyl n-, i-, s-, t-butylsulfinyl, methylsulfonyl, ethylsulfonyl n-, i-propylsulfonyl, n-, i-, s-, t-butylsulfonyl, trifluoromethyl, trichloromethyl, difluoromethyl, dichloromethyl, difluorochloromethyl, fluorodichloromethyl, trifluoromethoxy, trichloromethoxy, difluoromethoxy, dichloromethoxy, difluorochloromethoxy, fluorodichloromethoxy, trifluoromethylthio, trichloromethylthio, difluoromethylthio, dichloromethylthio, difluorochloromethylthio, fluorodichloromethylthio, trifluoromethylsulfinyl, trichloromethylsulfinyl difluoromethylsulfinyl, dichloromethylsulfinyl, difluorochloromethylsulfinyl, fluorodichloromethylsulfinyl, trifluoromethylsulfonyl, trichloromethylsulfonyl, difluoromethylsulfonyl dichloromethylsulfonyl, difluorochloromethylsulfonyl and fluorodichloromethylsulfonyl; in each case unsubstituted or mono- to trisubstituted benzyl or phenylethyl, where in each case the substituents are identical or different and are selected from the group consisting of fluorine, chlorine, bromine, iodine, cyano, nitro, methyl, ethyl, n-, i-propyl, n-, i-, s-, t-butyl, cyclopropyl, cyclobutyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfinyl, n-, i-, s-, t-butylsulfinyl, methylsulfonyl, ethylsulfonyl, n-, i-propylsulfonyl, n-, i-, s-, t-butylsulfonyl, trifluoromethyl, trichloromethyl, difluoromethyl, dichloromethyl, difluorochloromethyl, fluorodichloromethyl, trifluoromethoxy, trichloromethoxy, difluoromethoxy, dichloromethoxy, difluorochloromethoxy, fluorodichloromethoxy, trifluoromethylthio, trichloromethylthio, difluoromethylthio, dichloromethylthio, difluorochloromethylthio, fluorodichloromethylthio, trifluoromethylsulfinyl, trichloromethylsulfinyl, difluoromethylsulfinyl, dichloromethylsulfinyl, difluorochloromethylsulfinyl, fluorodichloromethylsulfinyl, trifluoromethylsulfonyl, trichloromethylsulfonyl, difluoromethylsulfonyl, dichloromethylsulfonyl, difluorochloromethylsulfonyl, fluorodichloromethylsulfonyl, n represents 1, 2, 3, 4, 5 or 6, where the group $C(R^1)R^2$ may be identical or different, when n is greater than 1, and when n represents 1, $R^1$ and $R^2$ furthermore together represent —$(CH_2)_2$—, —$(CH_2)_3$—, —$(CH_2)_4$—, —$(CH_2)_5$—, $R^1$ furthermore represents together with $R^3$ or $R^5$ —$(CH_2)_3$—, —$(CH_2)_4$—, —$(CH_2)_5$—, $R^3$ and $R^4$ furthermore together represent —$(CH_2)_4$—, —$(CH_2)_5$—, —$(CH_2)_6$—, $R^3$ and $R^5$ furthermore together represent —$(CH_2)_2$—, —$(CH_2)_3$—, —$(CH_2)_4$—, $R^5$ and $R^6$ furthermore together represent —$(CH_2)_4$—, —$(CH_2)_5$—, —$(CH_2)_6$—.

Very particularly preferred as starting material are amino alcohols of the formula (II), in which $R^1$ and $R^2$ in each case independently of one another represent hydrogen, methyl, ethyl, n-, i-propyl, n-, i-, s-, t-butyl cyclopropyl, cyclopentyl, cyclohexyl, cyclopropylmethyl, cyclopentylmethyl, cyclohexylmethyl, hydroxymethyl, hydroxyethyl; unsubstituted or mono- to trisubstituted phenyl, where the substituents are identical or different and are selected from the group consisting of fluorine, chlorine, bromine, iodine, cyano, nitro, methyl ethyl n-, i-propyl n-, i-, s-, t-butyl, cyclopropyl cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfinyl, n-, i-, s-, t-butylsulfinyl, methylsulfonyl, ethylsulfonyl, n-, i-propylsulfonyl, n-, i-, s-, t-butylsulfonyl, trifluoromethyl, difluoromethyl, trifluoromethoxy, difluoromethoxy, trifluoromethylsulfinyl, trifluoromethylsulfonyl, trifluoromethylcarbonyl, carboxyl, methoxycarbonyl, methoxymethyl ethoxyethyl, methoxyethyl ethoxymethyl, methylcarbonyl, ethylcarbonyl, phenylcarbonyl, phenoxycarbonyl, amino, methylamino, ethylamino, propylamino, dimethylamino, diethylamino; phenyl, which is substituted at two adjacent carbon atoms by —$(CH_2)_3$—, —$(CH_2)_4$—, —$OCH_2O$—, —$O(CH_2)_2O$—; unsubstituted or mono-to trisubstituted benzyl, where the substituents are identical or different and are selected from the group consisting of halogen, cyano, nitro, methyl, ethyl, n-, i-propyl n-, i-, s-, t-butyl, cyclopropyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfinyl n-, i-, s-, t-butylsulfinyl methylsulfonyl ethylsulfonyl, n-, i-propylsulfonyl n-, i-, s-, t-butylsulfonyl, trifluoromethyl, difluoromethyl, trifluoromethoxy, difluoromethoxy, trifluoromethylsulfinyl, trifluoromethylsulfonyl;

$R^3$ and $R^4$ independently of one another represent hydrogen, methyl, ethyl, n-, i-propyl, n-, i-, s-, t-butyl, $R^5$ and $R^6$ independently of one another represent hydrogen, methyl, ethyl, n-, i-propyl, n-, i-, s-, t-butyl, unsubstituted or mono- to trisubstituted phenyl, where the substituents are identical or different and are selected from the group consisting of fluorine, chlorine, bromine, iodine, cyano, nitro, methyl, ethyl, n-, i-propyl, n-, i-, s-, t-butyl, cyclopropyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl, ethylsulfinyl, n-, i-propylsulfinyl, n-, i-, s-, t-butylsulfinyl, methylsulfonyl ethylsulfonyl, n-, i-propylsulfonyl n-, i-, s-, t-butylsulfonyl, trifluoromethyl difluoromethyl, trifluoromethoxy, difluoromethoxy, trifluoromethylsulfinyl trifluoromethylsulfonyl; unsubstituted or mono- to trisubstituted benzyl, where the substituents are identical or different and are selected from the group consisting of fluorine, chlorine, bromine, iodine, cyano, nitro, methyl ethyl n-, i-propyl n-, i-, s-, t-butyl, cyclopropyl, cyclopentyl, cyclohexyl, methoxy, ethoxy, n-, i-propoxy, n-, i-, s-, t-butoxy, methylthio, ethylthio, n-, i-propylthio, n-, i-, s-, t-butylthio, methylsulfinyl ethylsulfinyl, n-, i-propylsulfinyl, n-, i-, s-, t-butylsulfinyl methylsulfonyl, ethylsulfonyl, n-, i-propylsulfonyl n-, i-, s-, t-butylsulfonyl trifluoromethyl, difluoromethyl trifluoromethoxy, difluoromethoxy, trifluoromethylsulfinyl, trifluoromethylsulfonyl, n represents 1, 2, 3 or 4, where the group $C(R^1)R^2$ may be identical or different, when n is greater than 1, and when n represents 1, $R^1$ and $R^2$ furthermore together represent —$(CH_2)_2$—, —$(CH_2)_3$—, —$(CH_2)_4$—, —$(CH_2)_5$—, $R^1$ furthermore represents together with $R^3$ or $R^5$ —$(CH_2)_3$—, —$(CH_2)_4$—, —$(CH_2)_5$—, $R^3$ and $R^4$ furthermore together represent —$(CH_2)_4$—, —$(CH_2)_5$—, —$(CH_2)_6$—, $R^3$ and $R^5$ furthermore together represent —$(CH_2)_2$—, —$(CH_2)_3$—, —$(CH_2)_4$—, $R^5$ and $R^6$ furthermore together represent —$(CH_2)_4$—, —$(CH_2)_5$—, —$(CH_2)_6$—.

Amino alcohols of the formula (II) are widely known and/or can be prepared according to known methods.

The formula (IV) provides a general definition of the mercaptans or salts thereof required as starting materials for carrying out the second step of the process according to the invention.

Preferred as starting material are mercaptans or salts thereof of the formula (IV), in which R represents unsubstituted or mono- or polysubstituted $C_1$-$C_{12}$-alkyl where the substituents are identical or different and are selected from the group consisting of fluorine, chlorine, bromine, iodine, hydroxy, $C_1$-$C_4$-alkoxy, halo-$C_1$-$C_4$-alkoxy having 1 to 9 identical or different fluorine, chlorine and/or bromine atoms, $C_1$-$C_4$-alkylthio, $C_1$-$C_4$-alkylsulfinyl and $C_1$-$C_4$-alkylsulfonyl; unsubstituted or mono- or polysubstituted $C_3$-$C_6$-cycloalkyl or $C_3$-$C_6$-cycloalkyl-$C_1$-$C_2$-alkyl, where the substituents are identical or different and are selected from the group consisting of fluorine, chlorine, bromine, iodine, $C_1$-$C_4$-alkyl and $C_1$-$C_4$-alkoxy; unsubstituted or mono- to pentasubstituted phenyl, where the substituents are identical or different and are selected from the group consisting of fluorine, chlorine, bromine, iodine, $C_1$-$C_4$-alkyl, $C_3$-$C_6$-cycloalkyl, $C_1$-$C_4$-alkoxy, halo-$C_1$-$C_4$-alkyl, halo-$C_1$-$C_4$-alkoxy, each having 1 to 9 identical or different fluorine, chlorine and/or bromine atoms; unsubstituted or mono- to pentasubstituted phenyl-$C_1$-$C_2$-alkyl, where the substituents are identical or different and are selected from the group consisting of fluorine, chlorine, bromine, iodine and $C_1$-$C_4$-alkyl; naphthyl; unsubstituted or mono- or polysubstituted heteroaryl (preferably furyl, thienyl, pyrrolyl, oxazolyl, oxazolinyl, isoxazolyl, thiazolyl, isothiazolyl, imidazolyl, pyrazolyl, 1,2,4-oxadiazolyl, 1,3,4-oxadiazolyl, 1,2,4-thiadiazolyl, 1,3,4-thiadiazolyl, 1,2,3-thiadiazolyl, 1,2,5-thiadiazolyl, 1,2,3-triazolyl, 1,2,4-triazolyl, tetrazolyl, pyridinyl, pyrimidinyl, pyridazinyl, pyrazinyl, triazinyl), where the substituents are identical or different and are selected from the group consisting of fluorine, chlorine, bromine, iodine, $C_1$-$C_4$-alkyl, $C_1$-$C_4$-alkoxy, unsubstituted or mono- to pentasubstituted phenyl, where the substituents are identical or different and are selected from the group consisting of fluorine, chlorine, bromine, iodine and $C_1$-$C_4$-alkyl, M represents hydrogen, ammonium or an alkali metal atom (preferably sodium, potassium, lithium and caesium).

Particularly preferred as starting material are mercaptans or salts thereof of the formula (IV), in which R represents in each case unsubstituted or mono- or polysubstituted methyl, ethyl n-, i-propyl, n-, i-, s-, t-butyl, in each case the isomeric pentyls, hexyl, octyl, decyls and dodecyls, where the substituents are identical or different and are selected from the group consisting of fluorine, chlorine, bromine, iodine, hydroxy, methoxy, ethoxy, n-, i-propoxy, n-, i-, s-, t-butoxy, trifluoromethoxy, trichloromethoxy, difluoromethoxy, dichloromethoxy, difluorochloromethoxy, fluorodichloromethoxy, methylthio, ethylthio, n-, i-propylthio, n-, i-, s-, t-butylthio, methylsulfinyl ethylsulfinyl, n-, i-propylsulfinyl, n-, i-, s-, t-butylsulfinyl, methylsulfonyl, ethylsulfonyl n-, i-propylsulfonyl, n-, i-, s-, t-butylsulfonyl; in each case unsubstituted or mono- or poly-substituted cyclopropyl, cyclobutyl, cyclopentyl, cyclohexyl, cyclopropylmethyl, cyclobutylmethyl cyclopentylmethyl, cyclohexylmethyl, cyclopropylethyl, cyclobutylethyl, cyclopentylethyl, cyclohexylethyl, where the substituents are identical or different and are selected from the group consisting of fluorine, chlorine, bromine, iodine, methyl, ethyl, n-, i-propyl n-, i-, s-, t-butyl, methoxy, ethoxy, n-, i-propoxy, n-, i-, s-, t-butoxy; unsubstituted or mono- to trisubstituted phenyl, where the substituents are identical or different and are selected from the group consisting of fluorine, chlorine, bromine, iodine, methyl, ethyl, n-, i-propyl, n-, i-, s-, t-butyl, cyclopropyl cyclobutyl, cyclopentyl, cyclohexyl, methoxy, ethoxy, n-, i-propoxy, n-, i-, s-, t-butoxy, trifluoromethyl, trichloromethyl, difluoromethyl, dichloromethyl, difluorochloromethyl, fluorodichloromethyl, trifluoromethoxy, trichloromethoxy, difluoromethoxy, dichloromethoxy, difluorochloromethoxy, fluorodichloromethoxy, in each case unsubstituted or mono- to trisubstituted benzyl or phenylethyl, where in each case the substituents are identical or different and are selected from the group consisting of fluorine, chlorine, bromine, iodine and methyl, ethyl, n-, i-propyl, n-, i-, s-, t-butyl; naphthyl; in each case unsubstituted or mono- or polysubstituted furyl thienyl, pyrrolyl, oxazolyl, oxazolinyl, isoxazolyl thiazolyl isothiazolyl imidazolyl, pyrazolyl, 1,2,4 oxadiazolyl, 1,3,4-oxadiazolyl, 1,2,4-thiadiazolyl, 1,3,4-thiadiazolyl, 1,2,3-thiadiazolyl, 1,2,5-thiadiazolyl, 1,2,3-triazolyl 1,2,4-triazolyl, tetrazolyl pyridinyl, pyrimidinyl, pyridazinyl, pyrazinyl, triazinyl, where in each case the substituents are identical or different and are selected from the group consisting of fluorine, chlorine, bromine, iodine, methyl, ethyl, n-, i-propyl n-, i-, s-, t-butyl, methoxy, ethoxy, n-, i-propoxy, n-, i-, s-, t-butoxy, unsubstituted or mono- to trisubstituted phenyl, where the substituents are identical or different and are selected from the group consisting of fluorine, chlorine, bromine, iodine and methyl, ethyl, n-, i-propyl, n-, i-, s-, t-butyl, M represents hydrogen, ammonium, sodium, potassium, lithium and caesium.

Very particularly preferred as starting material are mercaptans or salts thereof of the formula (IV), in which R represents in each case unsubstituted or mono or polysubstituted methyl, ethyl, n-, i-propyl, n-, i-, s-, t-butyl, in each case the isomeric pentyls, hexyl octyl, decyls and dodecyls, where the substituents are identical or different and are selected from the group consisting of fluorine, chlorine, bromine, iodine, hydroxy, methoxy, ethoxy, n-, i-propoxy, n-, i-, s-, t-butoxy, trifluoromethoxy, trichloromethoxy, methylthio, ethylthio, n-, i-propylthio, t-butylthio, methylsulfinyl, ethylsulfinyl, n-, i-propylsulfinyl, t-butylsulfinyl, methylsulfonyl, ethylsulfonyl, n-, i-propylsulfonyl, t-butylsulfonyl; in each case unsubstituted or mono- or polysubstituted cyclopropyl, cyclopentyl, cyclohexyl, cyclopropylmethyl, cyclopentylmethyl, cyclohexylmethyl, where the substituents are identical or different and are selected from the group consisting of fluorine, chlorine, bromine, iodine, methyl, ethyl, n-, i-propyl, t-butyl, methoxy, ethoxy, n-, i-propoxy, t-butoxy; unsubstituted or mono- to trisubstituted phenyl, where the substituents are identical or different and are selected from the group consisting of fluorine, chlorine, bromine, iodine, methyl, ethyl, n-, i-propyl, n-, i-, s-, t-butyl, cyclopropyl, cyclopentyl, cyclohexyl, methoxy, ethoxy, n-, i-propoxy, n-, i-, s-, t-butoxy, trifluoromethyl, difluoromethyl, trifluoromethoxy, unsubstituted or mono- to tnsbstituted benzyl, where the substituents are identical or different and are selected from the group consisting of fluorine, chlorine, bromine, iodine and methyl, ethyl, n-, i-propyl, n-, i-, s-, t-butyl; naphthyl; in each case unsubstituted or mono- or polysubstituted furyl, thienyl, pyrrolyl, oxazolyl, oxazolinyl, isoxazolyl, thiazolyl, isothiazolyl, imidazolyl, pyrazolyl, 1,2,4-oxadiazolyl, 1,3,4-oxadiazolyl, 1,2,4-thiadiazolyl, 1,3,4-thiadiazolyl, 1,2,3-thiadiazolyl, 1,2,5-thiadiazolyl, 1,2,3-triazolyl, 1,2,4-triazolyl, tetrazolyl, pyridinyl, pyrimidinyl, pyridazinyl, pyrazinyl, triazinyl, where in each case the substituents are identical or different and are selected from the group consisting of fluorine, chlorine, bromine, methyl, ethyl, n-, i-propyl, n-, i-, s-, t-butyl, methoxy, ethoxy, n-, i-propoxy, n-, i-, s-, t-butoxy, unsubstituted or mono- to trisubstituted phenyl, where the substituents are identical or different and are selected from the group consitg of fluorine, chlorine, bromine and methyl, ethyl, n-, i-propyl, n-, i-, s-, t-butyl, M represents hydrogen, ammonium, sodium and potassium.

Mercaptans or salts thereof of the formula (IV) are widely known and/or can be prepared according to known methods.

Saturated or unsaturated hydrocarbon radicals, e.g. alkyl and alkenyl, can in each case be straight-chain or branched as far as this is possible, including in combination with heteroatoms, e.g. in alkoxy.

Optionally substituted radicals may be mono- or polysubstituted, where in the case of polysubstitution the substituents may be identical or different.

Radicals substituted by halogen, e.g. haloalkyl, are mono- or polysubstituted up to perhalogenation. In the case of multiple halogenation the halogen atoms may be identical or different Halogen represents fluorine, chlorine, bromine or iodine.

However, it is also possible to combine the above-mentioned general or preferred radical definitions or illustrations with one another as desired, i.e. between the respective ranges and preferred ranges. The definitions apply both to the end products and, correspondingly, to the precursors and intermediates.

The first step of the reaction according to the invention can be carried out by addition of the amino alcohols of the formula (II) into the oleum. This procedure is preferably carried out with mechanical stirring in that way, that the added amino alcohol does not touch the glass surface of the reaction vessel.

The addition of the amino alcohol of the formula (II) into the oleum is preferably done with cooling to keep the temperature below 150° C., while a temperature range between 80° C. and 90° C. is particularly preferred In general a carbonization will not be observed even if higher substituted amino alcohols are employed.

The amino alcohols are applied in liquid form. Solutions with up to 15% water may also be used.

According to the invention oleum means a solution of sulphur trioxide ($SO_3$) in sulphuric acid. The content of $SO_3$ can be varied in a broad range. In general between 1% and 70% $SO_3$ are used. Preferably the reaction is carried out using between 15% and 60%, particularly preferably 15% and 30%, very particularly preferably 20% SO$_3$. For example, 40% oleum means that 100 g of this solution contains 40 g of SO$_3$.

The reaction temperatures employed to the first step of the reaction according to the invention may be varied over a broad range. In general the reaction is carried out between 50° C. and 200° C., preferably between 70° C. and 180° C., particularly preferably between 80° C. and 130° C.

The first step of the reaction is expediently carried out under atmospheric pressure, although it is also possible to work under reduced or elevated pressure. Particular preference is given to carrying out the reaction under atmospheric pressure.

The reaction time can be different depending on the scale of the reaction and may vary between 10 min and 4 hours.

The first step of the process is carried out in practice by reacting, for example, 1 mol of an amino alcohol of formula (II) with between 0.01 and 6 mol, preferably between 0.05 and 3 mol, particularly preferably between 0.1 and 1 mol, very particularly between 0.2 and 0.8 mol, especially preferably 0.6 mol of SO$_3$, which is applied as solution in sulphuric acid (i.e. oleum, see above).

The sulphuric acid esters of the formula (III) may be isolated. Preferably these esters of formula (III) are used without isolation for the conversion in the second step of the process according to the invention.

The second step of the reaction according to the invention can be carried out by addition of the mercaptans or salts thereof of formula (IV), if as salt, then preferably in form of an aqueous solution of said mercaptan salt, into of the sulphuric acid ester of formula (III). Before this addition the reaction mixture is diluted with water and neutralized with a base. The reaction mixture may be neutralized directly when the reaction is carried out in small scale, for example in laboratory scale. The addition of the mercaptans or salts thereof of formula (IV) is done between 10 min up to 24 h, depending on the scale of the reaction, preferably between 20 min and 12 h, particularly preferably between 30 min and 6 h.

The second step of the process is carried out in the presence of a base. Examples which may be mentioned are: alkali metal and alkaline earth metal hydroxides, such as NaOH, KOH, Ca(OH)$_2$, alkali metal carbonates or hydrogencarbonates, such as Na$_2$CO$_3$, Li$_2$CO$_3$, K$_2$CO$_3$, Cs$_2$CO$_3$ or NaHCO$_3$ and KHCO$_3$. Preference is given to Na$_2$CO$_3$, KOH, NaOH and NaHCO$_3$, in particular NaOH.

The reaction temperatures employed to the second step of the reaction according to the invention may be varied over a broad range. In general the reaction is carried out between 30° C. and 150° C., preferably between 50° C. and 120° C., particularly preferably between 60° C. and 80° C.

The second step of the reaction is expediently carried out under atmospheric pressure, although it is also possible to work under reduced or elevated pressure. Particular preference is given to carrying out the reaction under atmospheric pressure.

The second step of the reaction according to the invention may be carried out in the presence of a further diluent, where all customary inert organic solvents apply. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, tetrachloromethane, dichlorethane or trichloroethane; ethers, such as diethyl ether, diisopropyl ether, methyl tert.-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

The second step of the process is carried out in practice by reacting, for example, 1 mol of an sulphuric acid ester of formula (III) with between 1 and 10 mol, preferably between 1 and 5 mol, particularly preferably between 1 and 3 mol of an mercaptan or salt thereof of formula (IV) in the presence of a base, to keep the pH value in general between pH 11 and 12.

The end-product can be isolated using standard procedures, e.g. cristallization, chromatography, extraction and distillation.

The process according to the invention is illustrated by the preparation examples given below.

PREPARATION EXAMPLES

Example 1

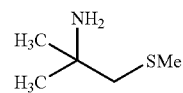

The oleum (120.1 g of 20% SO$_3$ in H$_2$SO$_4$, i.e. 0.3 mol=0.6 eq. SO$_3$) is placed in an 1 l flat-bottomed flask with flat-flange joint and the 2-amino-2-methyl-1-propanol (46.9 g, 0.5 mol=1 eq., 95%) is added slowly with mechanical stirring directly into the oleum so that 2-amino-2-methyl-1-propanol touches the glass surface of the flask. The temperature is maintained by cooling between 85° C. and 90° C. Stirring of the reaction mixture at 90° C. is continued for additional 30 min. After cooling to room temperature the mixture is first diluted with 200 ml of water and then 45% sodium hydroxide solution in water is added. The temperature in both procedures should not exceed 30° C. Under cooling the methyl mercaptane sodium salt solution (183.6 g, 0.5 mol=1 eq., 19.1% in water) is added and then stirring is continued at 60 to 65° C. for 6 h.

The mixture is cooled to 32° C. and all the following procedures are performed at this temperature. 100 ml methyl tert.-butyl ether is added, the mixture is stirred and the organic layer is separated. The aqueous layer is extracted with two 100 ml portions of tert.-butyl ether. The combined organic layers were dried over anhydrous sodium sulfate. After filtration the solvent was removed at 20° C. and under 150 mbar reduced pressure.

Yield: 62.7 g (crude product, purity according to internal standard: 68.8%, i.e. 72% of the theory) of 2-methyl-1-methylthio-2-propanamine.

[1]HANMR(d$_6$-DMSO): δ=1.04 (s, 6), 1.44 (broad, 2H), 2.10 (s, 3H), 2.48 (s, 2H) ppm. GC/MS-coupling: m/z (%)=104 (3) [M-15]$^+$, 58 (100), 42 (11), 41 (8), 31 (5).

Example 2

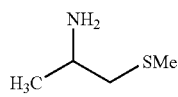

The oleum (91.4 g of 20% $SO_3$ in $H_2SO_4$, i.e. 0.23 mol=0.7 eq. $SO_3$) is placed in an 1 l flat-bottomed flask with flat-flange joint and the 2-aminopropanol (25.0 g, 0.33 mol=1 eq.) is added slowly with mechanical stirring directly into the oleum. The temperature is maintained by cooling slightly below 80° C. Stirring of the reaction mixture without heating is continued for additional 30 min. After cooling to room temperature the mixture is first diluted with 70 ml of water and then slowly 45% sodium hydroxide solution in water is added until a pH value of 11 is reached. The temperature in both procedures should not exceed 30° C. Under cooling the methyl mercaptane sodium salt solution (82.2 g, 0.33 mol=1 eq., 19.1% in water) is added and then stirring is continued at 60° C. for 12 h.

The mixture is cooled to 32° C. and all following procedures are performed at this temperature. 75 ml methyl tert.-butyl ether is added, the mixture is stirred and the organic layer is separated. The aqueous layer is extracted with two 75 ml portions of methyl tert.-butyl ether. The combined organic layers were dried over anhydrous sodium sulfate. After filtration the solvent was removed at 20° C. and under 150 mbar reduced pressure.

Yield: 23.3 g (62.2%, crude product, yield according to GC-purity) of 1-methylthio-2-propanamine.

$^1$H NMR ($d_6$-DMSO): δ=1.01 (d, 3H), 1.48 (broad, 2H), 2.04 (s, 3H), 2.38 (m, 2H), 2.90 (m, 1H) ppm.

GC/MS-coupling: m/z (%)=105 (4) [M]$^+$, 61 (5), 44 (100), 42 (12), 41 (5), 28 (4).

Example 3

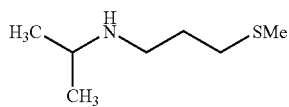

The oleum (45.4 g of 20% $SO_3$ in $H_2SO_4$, i.e. 0.114 mol=0.7 eq. $SO_3$) is placed in an 1 l flat-bottomed flask with flat-flange joint and the 3-(isopropylamino)-1-propanol (19.0 g, 0.16 mol=1 eq.) is added slowly with mechanical stirring directly into the oleum. The temperature is maintained by cooling slightly below 80° C. Stirring is continued for additional 60 min. After cooling to room temperature the mixture is first diluted under cooling with 70 ml of water and then slowly 45% sodium hydroxide solution in water is added until a pH value of 11 is reached. The temperature in both procedures should not exceed 30° C. Under cooling the methyl mercaptane sodium salt solution (59.5 g, 0.16 mol=1 eq., 19.1% in water) is added and then stirring is continued at 60° C. for 12 h.

The mixture is cooled to 32° C. and all following procedures are performed at this temperature. 75 ml methyl tert.-butyl ether is added, the mixture is stirred and the organic layer is separated. The aqueous layer is extracted with two 75 ml portions of methyl tert.-butyl ether. The combined organic layers were dried over anhydrous sodium sulfate. After filtration the solvent was removed at 20° C. and under 150 mbar reduced pressure.

Yield: 12.6 g (48.5%, crude product, yield according to GC-purity) of N-isopropyl-3-methylthio-1-propanamine.

$^1$H NMR ($d_6$-DMSO): δ=0.95 (d, 6H), 1.63 (m, 2H), 2.03 (s, 3H), 2.52 (m, 4H), 2.66 (m, 1H) ppm.

GC/MS-coupling: m/z (%)=147 (17) [M]$^+$, 132 (36), 89 (48), 72 (100), 58 (40), 30 (60).

Example 4

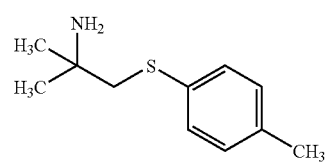

The oleum (28.4 g of 20% $SO_3$ in $H_2SO_4$, i.e. 0.07 mol 0.7 eq. $SO_3$) is placed in an 1 l flat-bottomed flask with flat-flange joint and the 2-amino-2-methylpropanol (9.4 g, 0.10 mol=1 eq.) is added slowly with mechanical stirring directly into the oleum. The temperature is maintained by cooling slightly below 80° C. Stirring without heating is continued for additional 30 min. After cooling to room temperature the mixture is first diluted with 30 ml of water and then slowly 45% sodium hydroxide solution in water is added until a pH value of 11 is reached. The temperature in both procedures should not exceed 30° C. Under cooling the 4-methyl thiophenol (12.4 g, 0.1 mol=1 eq.) is added and then stirring is continued at 60° C. for 12 h.

The mixture is diluted with 100 ml water, then 100 ml ethylacetate is added, the mixture is stirred and the organic layer is separated. The organic layer is washed twice with 50 ml portions of water. The organic layer is dried over anhydrous sodium sulfate. After filtration the solvent is removed at 20° C. and under 150 mbar reduced pressure.

Yield: 15.4 g (57.3%, crude product, yield according to GC-purity of 72.6%) of 2-methyl-1-[(4-methylphenyl)thio]-2-propanamine.

GC/MS-coupling: m/z (%)=195 (1) [M]$^+$, 138 (16), 58 (100).

Example 5

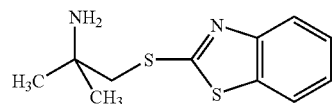

Applying the procedure according to example 4 the compound 1-(1,3-benzothiazol-2-ylthio)-2-methyl-2-propanamine is obtained.

Yield: 37.9% (according to GC-purity of 37.8%).

GC/MS-coupling: m/z (%)=238 (2) [M]$^+$, 181 (6), 148 (5), 108 (4), 58 (100), 28 (9).

Example 6

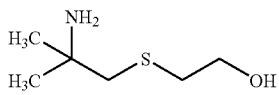

Applying the procedure according to example 4 the compound 2-[(2-amino-2-methylpropyl)thio]ethanol is obtained.

Yield: 24.8% (according to GC-purity of 74.0%).
GC/MS-coupling: m/z (%)=134 (2) [M-15]$^+$, 88 (3), 58 (100), 42 (7).

Example 7

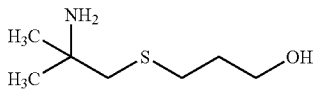

Applying the procedure according to example 4 the compound 3-[(2-amino-2-methylpropyl)thio]-1-propanol is obtained.

Yield: 57.9% (according to GC-purity of 71.6%).
GC/MS-coupling: m/z (%)=163 (1) [M]$^+$, 148 (1) [M$^+$–15], 58 (100), 42 (6).

Example 8

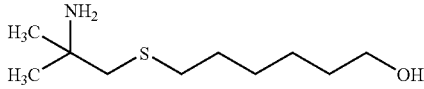

Applying the procedure according to example 4 the compound 6-[(2-amino-2-methylpropyl)thio]-1-hexanol is obtained.

Yield: 40.7% (according to GC-purity of 61.9%).
GC/MS-coupling: m/z (%)=205 (1) [M]$^+$, 190 (2), [M-15]$^{30}$, 58 (100), 41 (7).

What is claimed is:

1. A process for preparing compounds of formula (I)

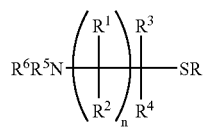

in which
R$^1$ and R$^2$ independently of one another represent hydrogen, C$_1$-C$_4$-alkyl, C$_3$-C$_8$-cycloakyl, C$_3$-C$_8$-cycloalkyl-C$_1$-C$_4$-alkyl, or hydroxy-C$_1$-C$_4$-alkyl; represent unsubstituted or mono- to pentasubstituted phenyl, where the substituents are identical or different and are selected from the group consisting of halogen, cyano, nitro, C$_1$-C$_4$-alkyl, C$_3$-C$_8$-cycloalkyl, C$_1$-C$_4$-alkoxy, C$_1$-C$_4$-alkylthio, C$_1$-C$_4$-alkylsulfinyl, C$_1$-C$_4$-alkylsulfonyl, carboxyl, C$_1$-C$_4$-alkoxycarbonyl, C$_1$-C$_4$-alkoxy -C$_1$-C$_4$-alkyl, C$_1$-C$_4$-alkylcarbonyl, halo-C$_1$-C$_4$-alkyl, halo-C$_1$-C$_4$-alkoxy, halo-C$_1$-C$_4$-alkylthio, halo-C$_1$-C$_4$-alkylsulfinyl, halo-C$_1$-C$_4$-alkylsulfonyl, halo-C$_1$-C$_4$-alkylcarbonyl, phenylcarbonyl, phenoxycarbonyl, amino, C$_1$-C$_4$-alkyl-amino, and di(C$_1$-C$_4$-alkyl)amino in which the alkyl groups can be identical or different; represent phenyl that is substituted at two adjacent carbon atoms by C$_3$-C$_4$-alkylene or C$_1$-C$_2$-alkylenedioxy; or represent unsubstituted or mono- to pentasubstituted phenyl-C$_1$-C$_4$-alkyl, where the substituents are identical or different and are selected from the group consisting of halogen, cyano, nitro, C$_1$-C$_4$-alkyl, C$_3$-C$_8$-cycloalkyl, C$_1$-C$_4$-alkoxy, C$_1$-C$_4$-alkylthio, C$_1$-C$_4$-alkylsulfinyl, C$_1$-C$_4$-alkylsulfonyl, halo-C$_1$-C$_4$-alkyl, halo-C$_1$-C$_4$-alkoxy, halo-C$_1$-C$_4$-alkylthio, halo-C$_1$-C$_4$-alkylsulfinyl, and halo-C$_1$-C$_4$-alkylsulfonyl;

R$^3$ and R$^4$ independently of one another represent hydrogen or C$_1$-C$_4$-alkyl, R$^5$ and R$^6$ independently of one another represent hydrogen or C$_1$-C$_4$-alkyl; represent unsubstituted or mono- to pentasubstituted phenyl, where the substituents are identical or different and are selected from the group consisting of halogen, cyano, nitro, C$_1$-C$_4$-alkyl, C$_3$-C$_8$-cycloalkyl, C$_1$-C$_4$-alkoxy, C$_1$-C$_4$-alkylthio, C$_1$-C$_4$-alkylsulfinyl, C$_1$-C$_4$-alkylsulfonyl, halo-C$_1$-C$_4$-alkyl, halo-C$_1$-C$_4$-alkoxy, halo-C$_1$-C$_4$-alkylthio, halo-C$_1$-C$_4$-alkylsulfinyl, and halo-C$_1$-C$_4$-alkylsulfonyl; or represent unsubstituted or mono- to penta-substituted phenyl-C$_1$-C$_4$-alkyl, where the substituents are identical or different and are selected from the group consisting of halogen, cyano, nitro, C$_1$-C$_4$-alkyl, C$_3$-C$_8$-cycloalkyl, C$_1$-C$_4$-alkoxy, C$_1$-C$_4$-alkylthio, C$_1$-C$_4$-alkylsulfinyl, C$_1$-C$_4$-alkylsulfonyl, halo-C$_1$-C$_4$-alkyl, halo-C$_1$-C$_4$-alkoxy, halo-C$_1$-C$_4$-alkylthio, halo-C$_1$-C$_4$-alkylsulfinyl, and halo-C$_1$-C$_4$-alkylsulfonyl, R represents unsubstituted or mono- or polysubstituted C$_1$-C$_{12}$-alkyl, where the substituents are identical or different and are selected from the group consisting of halogen, hydroxy, C$_1$-C$_4$-alkoxy, halo-C$_1$-C$_4$-alkoxy, C$_1$-C$_4$-alkylthio, C$_1$-C$_4$-alkylsulfinyl, and C$_1$-C$_4$-alkylsulfonyl; represents unsubstituted or mono- or polysubstituted C$_3$-C$_8$-cycloalkyl or C$_3$-C$_8$-cycloalkyl-C$_1$-C$_4$-alkyl, where the substituents are identical or different and are selected from the group consisting of halogen, C$_1$-C$_4$-alkyl, and C$_1$-C$_4$-alkoxy; represents unsubstituted or mono- to pentasubstituted phenyl, where the substituents are identical or different and are selected from the group consisting of halogen, C$_1$-C$_6$-alkyl, C$_3$-C$_8$-cycloalkyl, C$_1$-C$_4$-alkoxy, halo-C$_1$-C$_4$-alkyl, and halo-C$_1$-C$_4$-alkoxy; represents unsubstituted or mono- to pentasubstituted phenyl-C$_1$-C$_4$-alkyl, where the substituents are identical or different and are selected from the group consisting of halogen and C$_1$-C$_4$-alkyl; represents naphthyl; or represents unsubstituted or mono- or polysubstituted heteroaryl, where the substituents are identical or different and are selected from the group consisting of halogen, C$_1$-C$_4$-alkyl, C$_1$-C$_4$-alkoxy, and unsubstituted or mono- to pentasubstituted phenyl in which the substituents are identical or different and are selected from the group consisting of halogen and C$_1$-C$_4$-alkyl, and n represents 1, 2, 3, 4, 5, 6, 7, or 8, with the proviso that the group C(R$^1$)R$^2$ may be identical or different when n is greater than 1, with the further proviso that when n represents 1, $R^1$ and $R^2$ optionally together represent $C_2$-$C_5$-alkylene, $R^1$ together with $R^3$ or $R^5$ optionally represent $C_3$-$C_5$-alkylene, $R^3$ and $R^4$ optionally together represent $C_4$-$C_6$-alkylene, $R^3$ and $R^5$ optionally together represent $C_2$-$C_4$-alkylene, and $R^5$ and $R^6$ optionally together represent $C_4$-$C_6$-alkylene, comprising (1) reacting in a first step an amino alcohol of formula (II)

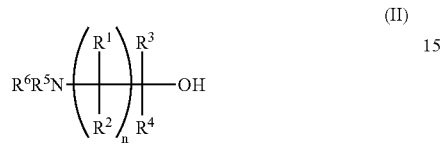

(II)

in which $R^1$, $R^2$, $R^3$, $R^4$, $R^5$, $R^6$ and n have the meanings given for formula (I), with oleum to give a sulphuric acid ester of formula (III)

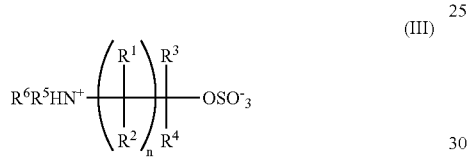

(III)

in which $R^1$, $R^2$, $R^3$, $R^4$, $R^5$, $R^6$, and n have the meanings given for formula (I), and (2) reacting in a second step the resultant sulphuric acid ester with a mercaptan of formula (IV)

RSM (IV)

or a salt thereof in which

R has the meanings given for formula (I), and

M represents hydrogen, ammonium, or an alkali metal atom, in the presence of a base and optionally in the presence of a diluent.

2. A process according to claim 1 wherein, for the compound of the formula (II), $R^1$ and $R^2$ independently of one another represent hydrogen, $C_1$-$C_4$-alkyl, $C_3$-$C_6$-cycloalkyl, $C_3$-$C_6$-cycloalkyl-$C_1$-$C_2$-alkyl, or hydroxy-$C_1$-$C_4$-alkyl; represent unsubstituted or mono- to pentasubstituted phenyl, where the substituents are identical or different and are selected from the group consisting of fluorine, chlorine, bromine, iodine, cyano, nitro, $C_1$-$C_4$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, carboxyl, $C_1$-$C_4$-alkoxycarbonyl, $C_1$-$C_4$-alkoxy-$C_1$-$C_4$-alkyl, $C_1$-$C_4$-alkylcarbonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl, halo-$C_1$-$C_4$-alkylsulfonyl, and halo-$C_1$-$C_4$-alkylcarbonyl, each halo-containing group having 1 to 9 identical or different fluorine, chlorine, and/or bromine atoms, phenylcarbonyl, phenoxycarbonyl, amino, $C_1$-$C_4$-alkylamino and di($C_1$-$C_4$-alkyl)amino in which the alkyl groups can be identical or different; represents phenyl that is substituted at two adjacent carbon atoms by $C_3$-$C_4$-alkylene or $C_1$-$C_2$-alkylenedioxy; represent unsubstituted or mono- to penta-substituted phenyl-$C_1$-$C_2$-alkyl, where the substituents are identical or different and are selected from the group consisting of fluorine, chlorine, bromine, iodine, cyano, nitro, $C_1$-$C_4$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl and halo-$C_1$-$C_4$-alkyl-sulfonyl, each halo-containing group having 1 to 9 identical or different fluorine, chlorine, and/or bromine atoms;

$R^3$ and $R^4$ independently of one another represent hydrogen or $C_1$-$C_4$-alkyl, $R^5$ and $R^6$ independently of one another represent hydrogen, $C_1$-$C_4$-alkyl, unsubstituted or mono- to pentasubstituted phenyl, where the substituents are identical or different and are selected from the group consisting of fluorine, chlorine, bromine, iodine, cyano, nitro, $C_1$-$C_4$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl, and halo-$C_1$-$C_4$-alkylsulfonyl, each halo-containing group having 1 to 9 identical or different fluorine, chlorine, and/or bromine atoms; unsubstituted or mono- to pentasubstituted phenyl-$C_1$-$C_2$-alkyl, where the substituents are identical or different and are selected from the group consisting of fluorine, chlorine, bromine, iodine, cyano, nitro, $C_1$-$C_4$-alkyl, $C_3$-$C_8$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, halo-$C_1$-$C_4$-alkyl, halo-$C_1$-$C_4$-alkoxy, halo-$C_1$-$C_4$-alkylthio, halo-$C_1$-$C_4$-alkylsulfinyl, and halo-$C_1$-$C_4$-alkylsulfonyl, each halo-containing group having 1 to 9 identical or different fluorine, chlorine, and/or bromine atoms; and n represents 1, 2, 3, 4, 5 or 6, with the proviso that the group $C(R^1)R^2$ may be identical or different when n is greater than 1, with the further proviso that when n represents 1, $R^1$ and $R^2$ optionally together represent $C_2$-$C_5$-alkylene, $R^1$ together with $R^3$ or $R^5$ optionally represent $C_3$-$C_5$-alkylene, $R^3$ and $R^4$ optionally together represent $C_4$-$C_6$-alkylene, $R^3$ and $R^5$ optionally together represent $C_2$-$C_4$-alkylene, and $R^5$ and $R^6$ optionally together represent $C_4$-$C_6$-alkylene.

3. A process according to claim 1 wherein, for the compound of the formula (IV), R represents unsubstituted or mono- or polysubstituted $C_1$-$C_{12}$-alkyl, where the substituents are identical or different and are selected from the group consisting of fluorine, chlorine, bromine, iodine, hydroxy, $C_1$-$C_4$-alkoxy, halo-$C_1$-$C_4$-alkoxy having 1 to 9 identical or different fluorine, chlorine, and/or bromine atoms, $C_1$-$C_4$-alkylthio, $C_1$-$C_4$-alkylsulfinyl, and $C_1$-$C_4$-alkylsulfonyl; represents unsubstituted or mono- or polysubstituted $C_3$-$C_6$-cycloalkyl or $C_3$-$C_6$-cycloalkyl-$C_1$-$C_2$-alkyl, where the substituents are identical or different and are selected from the group consisting of fluorine, chlorine, bromine, iodine, $C_1$-$C_4$-alkyl, and $C_1$-$C_4$-alkoxy; represents unsubstituted or mono- to pentasubstituted phenyl, where the substituents are identical or different and are selected from the group consisting of fluorine, chlorine, bromine, iodine, $C_1$-$C_4$-alkyl, $C_3$-$C_6$-cycloalkyl, $C_1$-$C_4$-alkoxy, halo-$C_1$-$C_4$-alkyl, halo-$C_1$-$C_4$-alkoxy, each halo-containing group having 1 to 9 identical or different fluorine, chlorine, and/or bromine atoms; represents unsubstituted or mono- to penta-substituted phenyl-$C_1$-$C_2$-alkyl, where the substituents are identical or different and are selected from the group consisting of fluorine, chlorine, bromine, iodine, and $C_1$-$C_4$-alkyl; represents naphthyl; or represents unsubstituted or mono- or polysubstituted heteroaryl, where the substituents are identical or different and are selected from the group consisting of fluorine, chlorine, bromine, iodine, $C_1$-$C_4$-alkyl, $C_1$-$C_4$-alkoxy, and unsubstituted or mono- to pentasubstituted phenyl in which the substituents are identical or different and are selected from the group consisting of fluorine, chlorine, bromine, iodine, and $C_1$-$C_4$-alkyl, and M represents hydrogen, ammonium, or an alkali metal atom.

4. A process according to claim 3 wherein R represents mono- or polysubstituted furyl, thienyl, pyrrolyl, oxazolyl, oxazolinyl, isoxazolyl, thiazolyl, isothiazolyl, imidazolyl, pyrazolyl, 1,2,4-oxadiazolyl, 1,3,4-oxadiazolyl, 1,2,4-thiadiazolyl, 1,3,4-thiadiazolyl, 1,2,3-thiadiazolyl, 1,2,5-thiadiazolyl, 1,2,3-triazolyl, 1,2,4-triazolyl, tetrazolyl, pyridinyl, pyrimidinyl, pyridazinyl, pyrazinyl, or triazinyl.

5. A process according to claim 3 wherein M represents sodium, potassium, lithium, or caesium.

6. A process according to claim 1 in which the oleum contains between 1% and 70% $SO_3$.

7. A process according to claim 1 in which the first step is carried out at a temperature of between 50° C. and 200° C.

8. A process according to claim 1 in which in the first step the amount of oleum provides between 0.01 and 6 mol of $SO_3$ as a solution in sulphuric acid per mol of the amino alcohol of formula (II).

9. A process according to claim 1 in which the sulphuric acid ester of formula (III) is reacted without isolation in the second step.

10. A process according to claim 1 in which the base used in the second step is an alkali metal or alkaline earth metal hydroxide or an alkali metal carbonate or hydrogen carbonate.

* * * * *